(12) United States Patent
Wang et al.

(10) Patent No.: US 8,883,994 B2
(45) Date of Patent: Nov. 11, 2014

(54) SWITCHABLE NUCLEIC ACID APTAMER PROBE AND USES THEREOF IN TUMOR LIVING CELL DETECTION AND IN VIVO DETECTION

(75) Inventors: Kemin Wang, Changsha (CN); Hui Shi, Changsha (CN); Xiaoxiao He, Changsha (CN); Xiaosheng Ye, Changsha (CN); Xu Wu, Changsha (CN); Qiuping Guo, Changsha (CN); Bing Zhou, Changsha (CN)

(73) Assignee: Hunan University, Changsha, Hunan (CN)

( * ) Notice: Subject to any disclaimer, the term of this patent is extended or adjusted under 35 U.S.C. 154(b) by 0 days.

(21) Appl. No.: 13/639,843

(22) PCT Filed: Mar. 22, 2011

(86) PCT No.: PCT/CN2011/072037
§ 371 (c)(1),
(2), (4) Date: Oct. 5, 2012

(87) PCT Pub. No.: WO2011/134328
PCT Pub. Date: Nov. 3, 2011

(65) Prior Publication Data
US 2013/0251638 A1    Sep. 26, 2013

(30) Foreign Application Priority Data

Apr. 26, 2010 (CN) .......................... 201010155148

(51) Int. Cl.
C07H 21/02     (2006.01)
C12Q 1/68      (2006.01)
C12P 19/34     (2006.01)
C07H 21/04     (2006.01)
C07H 21/00     (2006.01)
G01N 21/64     (2006.01)

(52) U.S. Cl.
CPC .......... *A61K 43/0054* (2013.01); *C12Q 1/6818* (2013.01); *G01N 21/6456* (2013.01); *C12Q 1/6886* (2013.01); *G01N 21/6428* (2013.01); *G01N 2021/6432* (2013.01)
USPC ....... 536/24.31; 435/6.1; 435/6.11; 435/91.1; 536/23.1; 536/24.3; 536/24.33; 536/25.3

(58) Field of Classification Search
USPC .................. 435/6.1, 6.11, 91.1; 436/94, 501; 536/23.1, 24.3, 24.33, 25.3, 24.31
See application file for complete search history.

(56) References Cited

U.S. PATENT DOCUMENTS

2003/0235828 A1* 12/2003 Gillibolian et al. ............... 435/6
2006/0199183 A1*  9/2006 Valat et al. ........................ 435/6
2009/0117549 A1*  5/2009 Tan et al. .......................... 435/6

OTHER PUBLICATIONS

Yang et el., Molecular beacon imaging of tumor marker gene expression in pancreatic cancer cells. Cancer Biology & Therapy, 4:5, 561-570, 2005.*
The Three-Dimensional Structure of DNA. Printed on Mar. 5, 2014.*

* cited by examiner

*Primary Examiner* — Frank Lu
(74) *Attorney, Agent, or Firm* — Raymond Y. Chan; David and Raymond Patent Firm

(57) ABSTRACT

A switch mode nucleic acid aptamer probe includes a probe main body, a fluorescence generating unit and a fluorescence quenching unit which are respectively connected to two ends of the probe main body. The probe main body includes a nucleic acid aptamer fragment with a function of specifically recognizing target tumor cell and a nucleic acid fragment linked to the nucleic acid aptamer fragment by a connection fragment with a length of 7~15 nm so as to form a hairpin structure. The ability of competitive hybridization of the nucleic acid fragment with the nucleic acid aptamer fragment is weaker than that of the target tumor cell. The use of the probe of the invention can be at least one of specific detection of tumor living cell in buffer solution, effective detection of tumor living cell in serum, and real-time fluorescence imaging and intravital detection of tumor in living body.

6 Claims, 4 Drawing Sheets

SEQUENCE LISTING

```
<160> NUMBER OF SEQ ID NOS: 10

<210> SEQ ID NO 1
<211> LENGTH: 66
<212> TYPE: DNA
<213> ORGANISM: Artificial Sequence
<220> FEATURE:
<223> OTHER INFORMATION: custom-designed and synthesized for the
      detection and imaging of target tumor cells

<400> SEQUENCE: 1
ctaaccgttt ttttttttt tttttatcta actgctgcgc cgccgggaaa atactgtacg      60
gttaga                                                               66

<210> SEQ ID NO 2
<211> LENGTH: 66
<212> TYPE: DNA
<213> ORGANISM: Artificial Sequence
<220> FEATURE:
<223> OTHER INFORMATION: custom-designed and synthesized as the negative
      control probe for the switchable nucleic acid aptamer probe

<400> SEQUENCE: 2
acggttagtt ttttttttt tttttatacg gtgacgtcgc cgccgggaaa atactgtcta      60
accgta                                                               66

<210> SEQ ID NO 3
<211> LENGTH: 41
<212> TYPE: DNA
<213> ORGANISM: Artificial Sequence
<220> FEATURE:
<223> OTHER INFORMATION: custom-designed and synthesized for the
      recognition of target tumor cells

<400> SEQUENCE: 3
atctaactgc tgcgccgccg ggaaaatact gtacggttag a                        41
```

-continued

```
<210> SEQ ID NO 4
<211> LENGTH: 41
<212> TYPE: DNA
<213> ORGANISM: Artificial Sequence
<220> FEATURE:
<223> OTHER INFORMATION: custom-designed and synthesized as the negative
      control probe for the nucleic acid aptamer peobe

<400> SEQUENCE: 4
atacggtgac tgcgccgccg ggaaaatact gtctaaccgt a                    41

<210> SEQ ID NO 5
<211> LENGTH: 48
<212> TYPE: DNA
<213> ORGANISM: Artificial Sequence
<220> FEATURE:
<223> OTHER INFORMATION: custom-designed and synthesized for the
      recognition of target tumor cells

<400> SEQUENCE: 5
aacaccgtgg aggatagttc ggtggctgtt cagggtctcc tcccggtg             48

<210> SEQ ID NO 6
<211> LENGTH: 39
<212> TYPE: DNA
<213> ORGANISM: Artificial Sequence
<220> FEATURE:
<223> OTHER INFORMATION: custom-designed and synthesized for the
      recognition of target tumor cells

<400> SEQUENCE: 6
agtccatttt attcctgaat atttgttaac ctcatggac                       39

<210> SEQ ID NO 7
<211> LENGTH: 17
<212> TYPE: DNA
<213> ORGANISM: Artificial Sequence
<220> FEATURE:
<223> OTHER INFORMATION: custom-designed and synthesized as the
      connecting fragment

<400> SEQUENCE: 7
tttttttttt ttttttt                                               17

<210> SEQ ID NO 8
<211> LENGTH: 8
<212> TYPE: DNA
<213> ORGANISM: Artificial Sequence
<220> FEATURE:
<223> OTHER INFORMATION: custom-designed and synthesized as the nucleic
      acid fragment

<400> SEQUENCE: 8 ctaaccgt                                                         8

<210> SEQ ID NO 9
<211> LENGTH: 41
<212> TYPE: DNA
<213> ORGANISM: Artificial Sequence
<220> FEATURE:
<223> OTHER INFORMATION: custom-designed and synthesized as the nucleic
      acid fragment wtich is completely complemented with SEQ ID NO 3

<400> SEQUENCE: 9
tctaaccgta cagtattttc ccggcggcgc agcagttaga t                    41

<210> SEQ ID NO 10
```

```
<211> LENGTH: 59
<212> TYPE: DNA
<213> ORGANISM: Artificial Sequence
<220> FEATURE:
<223> OTHER INFORMATION: random nucleic acid fragment without any
      labeling

<400> SEQUENCE: 10
ctaaccgttt ttttttttt tttttatcta actgctgcgc cgccgggaaa atactgtac     59
```

SWITCHABLE NUCLEIC ACID APTAMER PROBE AND USES THEREOF IN TUMOR LIVING CELL DETECTION AND IN VIVO DETECTION

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

1. Field of Invention

The present invention relates to the technical field of nucleic acid-based detection, and more particularly to a nucleic acid aptamer probe and use thereof in tumor detection.

2. Description of Related Arts

A tumor is a common disease threatening the health of a human body. An accurate immunophenotyping of tumor cells is advantageous in implementing an early diagnosis and therapy of the tumor cells, so that the cure rate of tumor is increased. Antigen-antibody reaction is the basis of immunodiagnosis. The rapid development of antibody technology in past years has made great contributions to tumor therapy and diagnosis research. However, the antibody technology has encountered unprecedented challenges since the appearance of nucleic acid aptamers.

Nucleic acid aptamers are synthetic oligodeoxynucleotides designed according to rigorous recognition and binding affinities between nucleotides, and are obtained by screening through systematic evolution of ligands by exponential enrichments (SELEX). Nucleic acid aptamers not only have features similar to antibodies, such as highly specific recognition and highly binding affinities to targets, but are also advantageous in many aspects. Such advantages include: a small molecular weight, non-immunogenicity, variety of targets (including enzyme, growth factor, antigen, gene regulator, cell adhesion molecule, complete tumor cell, and etc.), a simple synthesis process, good repeatability, flexible modification, convenient long period storage, and transport at normal temperature etc. These characteristics make the nucleic acid aptamers to be acknowledged and accepted as tumor diagnosis probes; tumor recognition and detection methods based on nucleic acid aptamers have gradually become a novel, widespread, and applicable technology which brings in a new spring for the development in the field of typing, diagnosis, and therapy of tumor cells.

In the disclosure of "Aptamers Evolved from Live Cells as Effective Molecular Probes for Cancer Study." Proc Nati Acad Sci USA 2006, 103 (32): 11838-11843; Dihua Shangguan, YingLi, ZhiwenTang, et al., a cell-SELEX strategy against whole living cells is disclosed. In this strategy a group of specific nucleic acid aptamers has been generated for the specific recognition of leukemia cells, and nucleic acid aptamers with fluorescence dye labelings are successfully used for effective recognition and detection of target leukemia cells mixed with normal human bone marrow aspirates. The research group further employs the cell-SELEX strategy to generate a series of nucleic acid aptamers for the specific recognition of tumor cells corresponding to lymphoma, liver cancer, lung cancer, and etc. These nucleic acid aptamers have been widely used for typing and detecting a variety of tumor cells or tissues. However, the current tumor detection method based on nucleic acid aptamers still mainly uses a single signal labeling means, such as fluorescent or radioactive labeling, in which the nucleic acid aptamers serve as target molecules and identify tumor cells through the binding affinity difference between the nucleic acid aptamers and the target and non-target cells. Since an inevitable non-specific adsorption exists between the nucleic acid aptamers and the non-target cells, this method cannot meet the requirement of a convenient, fast, highly specific and highly sensitive analysis of a complex mixture and thus implementation of an early diagnosis and development of a related therapy of the tumor in a clinical detection is limited.

SUMMARY OF THE PRESENT INVENTION

The technical problem to be solved according to the present invention is to provide a switchable nucleic acid aptamer probe with high stability, specificity, sensibility to overcome the disadvantages of the conventional art as well as to provide an application method, which is easy to operate, fast, sensitive, specific, and of low cost, for tumor living cell detection and in vivo detection by a switchable nucleic acid aptamer probe.

Additional advantages and features of the invention will become apparent from the description which follows, and may be realized by means of the instrumentalities and combinations particular point out in the appended claims.

According to the present invention, the foregoing and other objects and advantages are attained by a switchable nucleic acid aptamer probe, wherein the switchable nucleic acid aptamer probe comprises a probe body, with a fluorescence generating unit and a fluorescence quenching unit respectively connected to two ends of the switchable nucleic acid aptamer probe. The probe body comprises a nucleic acid aptamer fragment (Referred to as fragment 1) capable of specifically recognizing target tumor cells and a nucleic acid fragment (Referred to as fragment 2) capable of complementing the nucleic acid aptamer fragment with a complementary sequence (Continual) of 6~12 base pairs. The nucleic acid aptamer fragment and the nucleic acid fragment are connected by a connecting fragment (Referred to as fragment 3) of a length of 7~15 nm to form a hairpin structure. The ability of the nucleic acid fragment for competitively hybridizing with the nucleic acid aptamer fragment is weaker than the ability of the target tumor cells for interacting with the nucleic acid aptamer fragment. In this technical solution, fragment 1 is capable of specifically recognizing the target tumor cells. A main function of fragment 2, which is complemented with fragment 1 with a complementary sequence of 6~12 base pairs, is to partially hybridize with fragment 1 to form a stable hairpin structure while the hybridizing ability thereof does not interfere with the competitive binding between the target tumor cells and the fragment 1. The main function of fragment 3 is to connect fragment 1 and fragment 2 to form a probe body. The fragment 2 should be complemented with the sequence of fragment 1 adjacent to the fluorescence generating (quenching) unit at end thereof, so that the fluorescence generating unit and the fluorescence quenching unit at two ends of the probe are as close as possible.

In the above switchable nucleic acid aptamer probe, the fluorescence generating unit is preferably selected from the group consisting of fluorescence dye molecule and fluorescence nano-particle; the fluorescence quenching unit is preferably selected from the group consisting of fluorescence quenching group and functional nano-material having fluorescence quenching effect.

In the above switchable nucleic acid aptamer probe, the fluorescence dye molecule is preferably selected from the group consisting of fluorescein, rhodamine, and Cy5; the fluorescence nano-particle is preferably fluorescence dye-doped silica nano-particle or fluorescence quantum dot. The fluorescence quenching group is preferably selected from the group consisting of DABCYL, BHQ1, and BHQ2; the functional nano-material having fluorescence quenching effect is preferably gold nano-particle or carbon nano-tube. Person of ordinary skilled in the art can decide and choose the combination of the fluorescence generating unit and the fluorescence quenching unit by himself/herself. For example, the combination may be selected from the group consisting of fluorescein/DABCYL, fluorescein/BHQ1, tetramethylrhodamine/BHQ2, tetramethylrhodamine/gold nano-particle, Cy5/ gold nano-particle, Cy5/ carbon nano-tube, fluorescence dye-doped silica nano-particle/BHQ2, and fluorescence quantum dot/BHQ2.

In the above switchable nucleic acid aptamer probe, the nucleic acid aptamer fragment is preferably tumor-specific nucleic acid aptamer selected from the systematic evolution of ligands by exponential enrichment technology (SELEX technology for short). And more particularly, the nucleic acid aptamer fragment is selected from the group consisting of a nucleic acid aptamer sequence 1 which is capable of specifically recognizing human T Cell acute lymphoblastic leukemia cell lines (CCER-CEM tumor cells), a nucleic acid aptamer sequence 2 which is capable of specifically recognizing Human Burkitt's lymphoma cell lines (Ramos cells), and a nucleic acid aptamer sequence 3 which is capable of specifically recognizing mouse hepatoma cell lines (MEAR cells); wherein The nucleotide sequence of the nucleic acid aptamer fragment 1 is: SEQ ID NO: 3:5'-ATC TAA CTG CTG CGC CGC CGG GAA AAT ACT GTA CGG TTA GA-3';

The nucleotide sequence of the nucleic acid aptamer fragment 2 is: SEQ ID NO: 5:5'-AAC ACC GTG GAG GAT AGT TCG GTG GCT GTT CAG GGT CTC CTC CCG GTG-3';

The nucleotide sequence of the nucleic acid aptamer fragment 3 is: SEQ ID NO: 6:5'-AGT CCA TTT TAT TCC TGA ATA TTT GTT AAC CTC ATG GAC-3'.

In the above switchable nucleic acid aptamer probe, the connecting fragment is preferably selected from a group consisting of a fragment not capable of hybridizing with the nucleic acid aptamer fragment nor the nucleic acid fragment, and a fragment containing a polymer chain with hydrophilicity and biocompatibility (such as polyethylene glycol).

As an integral technical concept, the present invention further provides an application of the switchable nucleic acid aptamer probe in tumor living cell detection and in vivo detection, the application comprises at least one of the three detection process:

(1) Specific detection of tumor cells in a buffer;
(2) Effective detection of tumor cells in a serum;
(3) Real-time fluorescence imaging and in vivo detection of tumor cells in living objects.

In the above application, the detailed detection method of specific detection of tumor cells in a buffer is as follows: a 5~50 nM switchable nucleic acid aptamer probe is added into the buffer under detection, avoiding light, incubation for 15 min at room temperature in the dark, employing a flow cytometry to detect the fluorescence signal of the cells immediately, and statistically analyze the fluorescence intensity of the collected cell groups (for example 10,000 cells as a group). When the number of the cells with fluorescence intensity above 10 accounts for over 20% of the total number of the cells in the cell groups, it is assumed that the target tumor living cells in the buffer under detection are detected by the switchable nucleic acid aptamer probe.

In the above application, the detailed detection method of effective detection of tumor cells in a serum is as follows: a 5~50 nM switchable nucleic acid aptamer probe is added into the serum under detection, avoiding light, incubation for 30 min on ice in the dark, employing a flow cytometry to detect the fluorescence signal of the cells immediately, and statistically analyze the fluorescence intensity of the collected cell groups (for example 10,000 cells as a group). When the number of the cells with fluorescence intensity above 10 accounts for over 20% of the total number of the cells of the cell groups, it is assumed that the target tumor living cells in the serum under detection are detected by the switchable nucleic acid aptamer probe.

In the above application, the detailed detection method of real-time fluorescence imaging and in vivo detection of tumor cells in living objects is as follows: 0.3~0.5 nmol of a switchable nucleic acid aptamer probe and a oligonucleotide, of random sequence with a concentration above ten times higher than the concentration of the switchable nucleic acid aptamer probe, are intravenously injected into the living objects under detection. A whole-body fluorescence imaging system is employed to record in real-time the change of the fluorescence intensity of each site in the animal. When a fluorescence signal at a tissue is observed to be obviously higher than at other tissues (under the premise that the condition, in which the increase of the fluorescence intensity is not resulted from the switchable nucleic acid aptamer probe but is passively accumulated from metabolism-related tissues such as liver, heart, kidney, bladder, and etc., is excluded, as is known for the person ordinary skilled in the art), it is assumed that the target tumor living cells in the animal are detected by the switchable nucleic acid aptamer probe, and the sites of the tumor are at the positions with obviously increasing fluorescence signals.

The present invention has many advantages over the prior art. The present invention takes advantage of the specific highly binding affinity to tumor cells of the nucleic acid aptamer and highly sensitive signal conversion mechanism of the hairpin type nucleic acid probe to build up tumor living cells detection and in vivo detection technology based on the switchable nucleic acid aptamer probe (Aptamer-based Switchable Probe, ASP for short). The present invention takes the hairpin type nucleic acid probe as the signal conversion unit in ASP, which highly sensitively and specifically converts the specific recognition of the target tumors cells by the nucleic acid aptamer to an occurrence of fluorescence signal, thus avoiding the complex washing procedure for overcoming the non-specific binding signals in a detection method using nucleic acid aptamer based on single fluorescence labeling or radioactive, shortening the detection time, and expanding the applicable range of the detection systems. Simultaneously, according to the signal conversion mechanism of the hairpin type nucleic acid probe, the fluorescence signals shifted from non-generation to generation due to the conformation change before and after the ASP binding to the target tumor cells, the sensitivity and the specificity of the detection method are greatly improved. These advantages are incomparable to the conventional analytical methods. The nucleic acid aptamer in the technical solution of the present invention not only functions to select and recognize tumor cells, but also provides an important function for controlling the ASP signals shifted from "closed" to "open". Since the nucleic acid aptamer holds a relatively high selectivity when binding to the tumor cells, and furthermore, the design of the hairpin type nucleic acid probe makes a stronger binding affinity between the nucleic acid aptamer and the tumor cells required for conformation or signal conversion, so that ASP represents high selectivity and specificity to the target tumor cells and thus separation-free and real-time analytical detection of complex mixed system (e.g. serum) and even living objects can be achieved.

The present invention puts forward a novel means and concept for the application of nucleic acid aptamers in the study of tumor living cell detection and in vivo imaging. The detection and analysis operation of the tumor living cells and in vivo tumor tissues by the switchable nucleic acid aptamer probe is simple, fast, sensitive, specific, and of low cost. Thus the present invention reveals a great scientific value and broad market prospect, so that it may provide great social profit and economic profit.

Still further objects and advantages will become apparent from a consideration of the ensuing description and drawings.

These and other objectives, features, and advantages of the present invention will become apparent from the following detailed description, the accompanying drawings, and the appended claims.

Curve a represents a background fluorescence spectrum of a control physiological buffer;

Curve b represents a fluorescence spectrum of the switchable nucleic acid aptamer probe in the control physiological buffer;

Curve c represents a fluorescence spectrum of a switchable control nucleic acid probe in the control physiological buffer;

Curve d represents a fluorescence spectrum of the switchable control nucleic acid probe after incubation in physiological buffer containing nucleic acid fragments complemented with the switchable nucleic acid aptamer probe;

Curve e represents a fluorescence spectrum of a nucleic acid aptamer probe with single fluorescence labeling in the control physiological buffer;

Curve f represents a fluorescence spectrum of a control nucleic acid probe with single fluorescence labeling in the control physiological buffer; and Curve g represents a fluorescence spectrum of the switchable nucleic acid aptamer probe after incubation in physiological buffer containing nucleic acid fragments complemented with the switchable nucleic acid aptamer probe.

Figure 5:
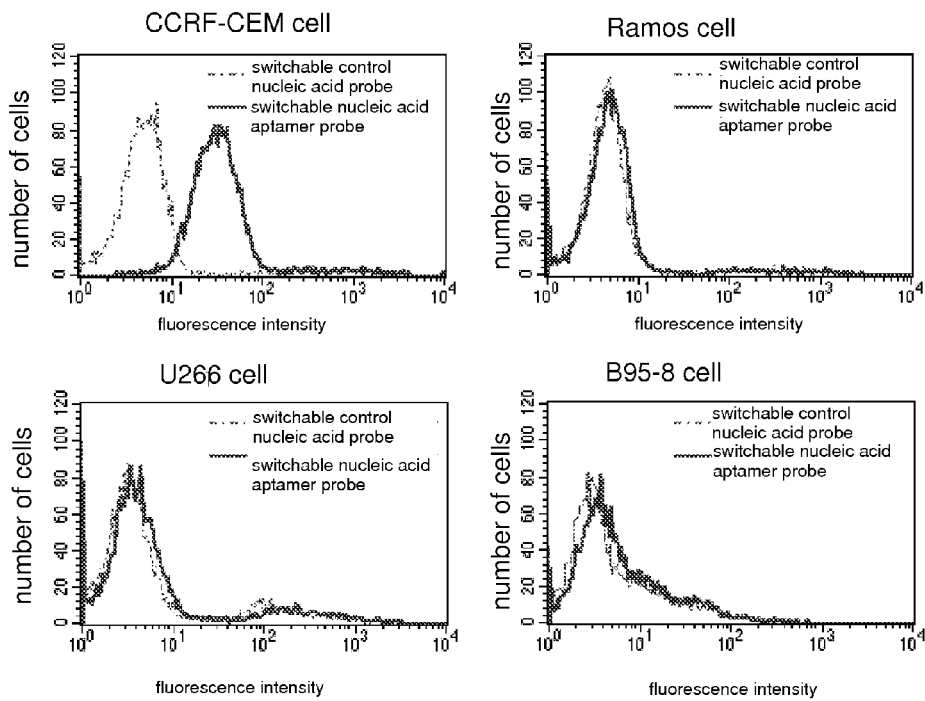

FIG. 5 is a comparison diagram of the detection results of different tumor cells buffer using the switchable nucleic acid aptamer probe and the switchable control nucleic acid probes according to a third preferred embodiment of the present invention.

Figure 6:
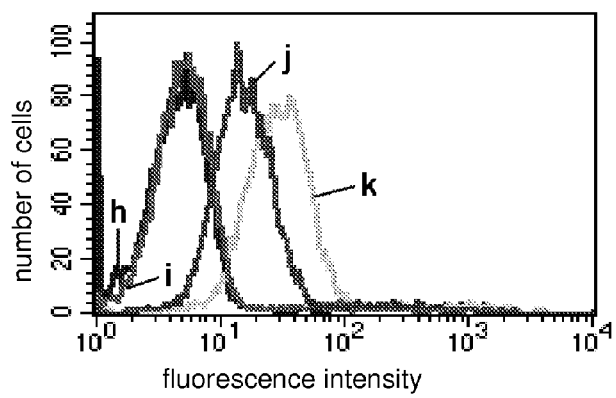

FIG. 6 is a comparison diagram of the detection sensitivity results of CCRF-CEM tumor cells in buffer using different kinds of probes according to a fourth preferred embodiment of the present invention, wherein:

Curve h represents the statistical analysis result of the fluorescence intensity of CCRF-CEM cells after incubation in buffer with the control nucleic acid probe with single fluorescence labeling;

Curve i represents the statistical analysis result of the fluorescence intensity of CCRF-CEM cells after incubation in buffer with switchable control nucleic acid probes;

Curve j represents the statistical analysis result of the fluorescence intensity of CCRF-CEM cells after incubation in buffer with the nucleic acid aptamer probe with single fluorescence labeling; and Curve k represents the statistical analysis result of the fluorescence intensity of CCRF-CEM cells after incubation in buffer with the switchable nucleic acid aptamer probe.

Figure 7:
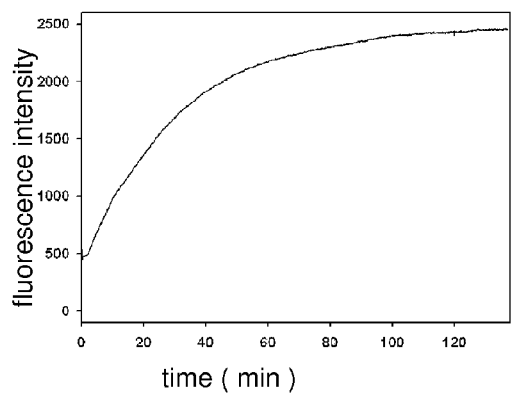

FIG. 7 is a diagram of the fluorescence stability investigation result of the switchable nucleic aptamer probe in serum according to a fifth preferred embodiment of the present invention.

Figure 8:
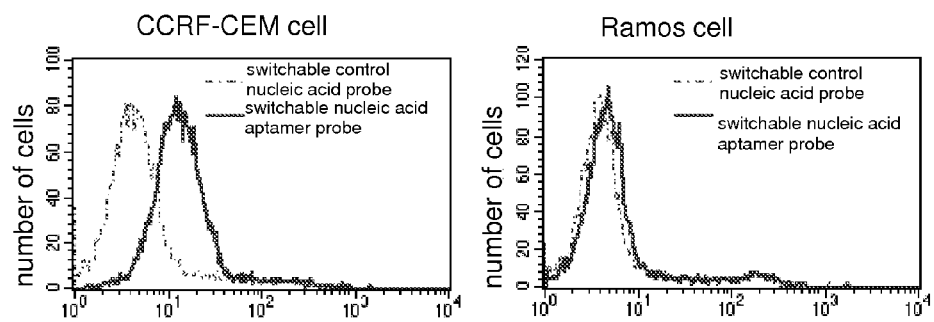

FIG. 8 is a diagram of the detection results of the specific recognition of different tumor cells using the switchable nucleic acid aptamer probe and the switchable control nucleic acid probe according to a sixth preferred embodiment of the present invention.

Figure 9:
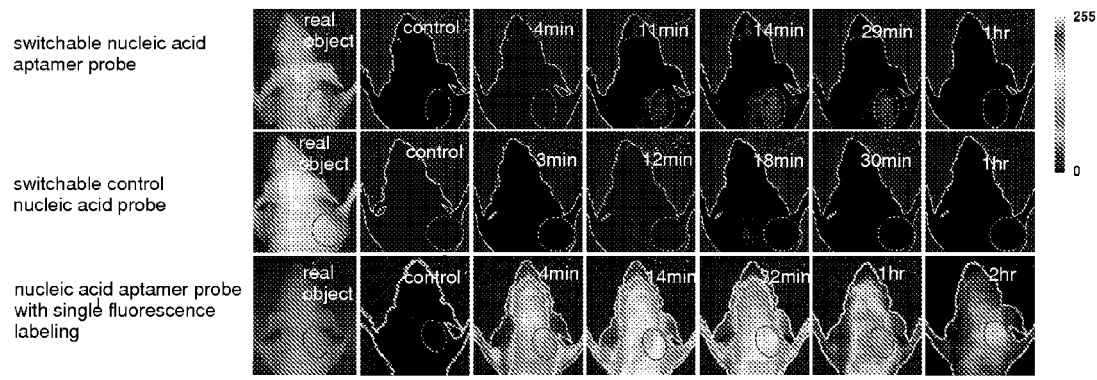

FIG. 9 is a comparison diagram of in vivo detection results of tumor cells in tumor-bearing nude mice using different type of probes, wherein the position of the circle indicates the position of the CCRF-CEM tumor.

Figure 10:
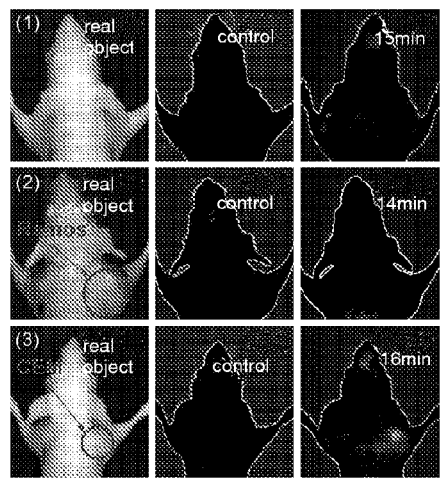

FIG. 10 is a comparison diagram of in vivo detection results of specific recognition of living tumor cells in nude mice with different cancer cells using the switchable nucleic acid aptamer probe according to an eighth preferred embodiment of the present invention, wherein:

Line 1 illustrates the fluorescence imaging result of the switchable nucleic acid aptamer probe in normal nude mice without tumors;

Line 2 illustrates the fluorescence imaging result of the switchable nucleic acid aptamer probe in Ramos tumor-bearing nude mice; and Line 3 illustrates the fluorescence imaging result of the switchable nucleic acid aptamer probe in CCRF-CEM tumor-bearing nude mice.

DETAILED DESCRIPTION OF THE PREFERRED EMBODIMENT

The following description is disclosed to enable any person skilled in the art to make and use the present invention. Preferable embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Embodiment 1

Figure 1:
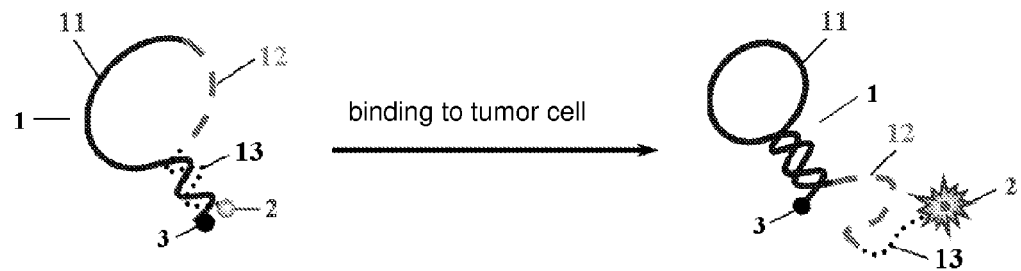
FIG. 1 is a schematic view illustrating the structures of a switchable nucleic acid aptamer probe before and after binding to tumor cells according to a first preferred embodiment of the present invention (in which the solid line represents a nucleic acid aptamer fragment, the broken line represents a connecting fragment, and the dotted line represents a nucleic acid fragment).

FIG. 1 is a schematic view illustrating the detecting principle of switchable nucleic acid aptamer probes designed for CCRF-CEM tumor cells.

A switchable nucleic acid aptamer probe, as illustrated in FIG. 1 of the drawings, comprises a probe body 1, a fluorigenic generating unit 2 and a fluorescence quenching unit 3, wherein the fluorigenic generating unit 2 and the fluorescence quenching unit 3 are respectively connected to two ends of the probe body 1. The probe body 1 comprises a nucleic acid aptamer fragment 11 with specific recognition ability to target tumor cells and a nucleic acid fragment 13 partially complemented with the nucleic acid aptamer fragment 11. The nucleic acid aptamer fragment 11 and the nucleic acid fragment 13 are connected by a connecting fragment 12 to form a hairpin structure. The ability of the nucleic acid fragment 13 to competitively interact with nucleic acid aptamer fragment 11 is weaker than the target tumor cells. The fluorigenic generating unit 2 may be fluorescence dye molecule Cy5 near-infrared fluorescence group which is connected to an end of the nucleic acid fragment 13. The fluorescence quenching unit 3 may be BHQ2 fluorescence quenching group which is connected to an end of the nucleic acid aptamer fragment 11. After the design is completed, the switchable nucleic acid aptamer probes in this preferred embodiment are designated to Takara Co., Ltd for synthesis production.

The nucleic acid aptamer fragment 11 in this preferred embodiment, which is a DNA fragment capable of specific recognizing CCRF-CEM tumor cell, has a nucleotide sequence of:

SEQ ID NO: 3: 5'-ATC TAA CTG CTG CGC CGC CGG GAA

AAT ACT GTA CGG TTA GA-3';

The connecting fragment 12 in this preferred embodiment, which is a DNA fragment polymerized by a plurality of thymine deoxynucleotides, has a nucleotide sequence of:

SEQ ID NO: 7: 5'-TTT TTT TTT TTT TTT TT-3';

The nucleic acid fragment 13 in this preferred embodiment, which is a DNA fragment partially complemented with the nucleic acid aptamer probe, has a nucleotide sequence of:

SEQ ID NO: 8: 5'-CTA ACC GT-3';

The above three fragments are orderly connected to form a switchable nucleic acid aptamer probe having a sequence of:

SEQ ID NO: 1: [5'-(Cy5)-CTA ACC GT TTT TTT TTT

TTT TTT TT ATC TAA CTG CTG CGC CGC CGG GAA AAT

ACT GTA CGG TTA GA-(BHQ2)-3'].

Figure 2:
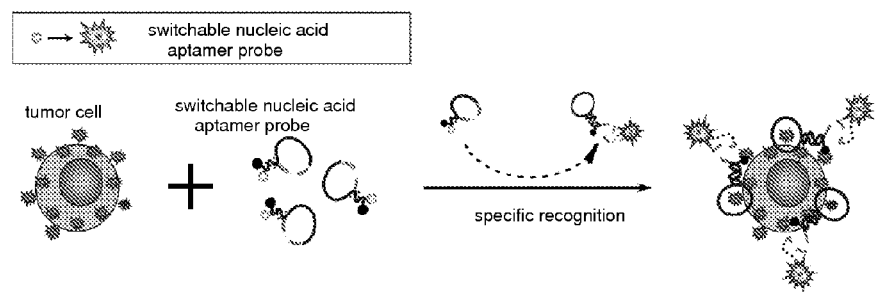
FIG. 2 is a schematic view illustrating the principle of detection of tumor cells using the switchable nucleic acid aptamer probe according to the above first preferred embodiment of the present invention.
Figure 3:
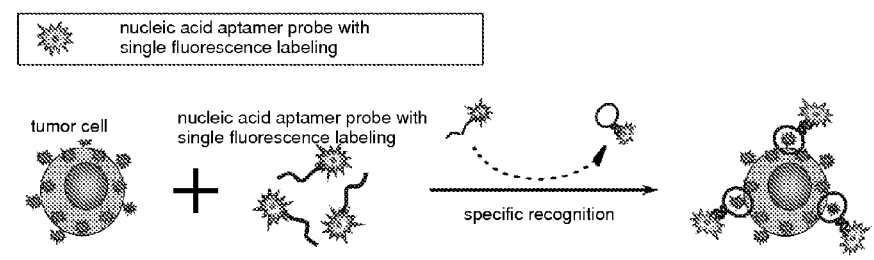
FIG. 3 is a schematic view illustrating the principle of detection of tumor cells by a nucleic acid aptamer probe based on a single fluorescence labeling according to the prior art.

The detection principle of the switchable nucleic acid aptamer probe in this preferred embodiment is illustrated in FIG. 2 of the drawings. When there is no CCRF-CEM tumor cell in the system under detection, the switchable nucleic acid aptamer probe mainly represents the hairpin conformation, and the fluorescence signal of the Cy5 near-infrared fluorescence group at one end is absorbed by the BHQ2 fluorescence quenching group at another end, so that the fluorescence signal is in a closed state. When the switchable nucleic acid aptamer probe is specifically bond to the CCRF-CEM tumor cells, the conformation of the nucleic acid aptamer is changed and the hairpin conformation is destroyed, so that an obvious recovery of fluorescence is presented and thus the fluorescence signal is in an open state. Since the change of the conformation only takes place when the nucleic acid aptamer fragment 11 is specifically bonded to the CCRF-CEM tumor cells, while the fluorescence signal without binding to the CCRF-CEM tumor cells is maintained in the closed state, the detecting background is low and thus a highly specific, highly sensitive, and separation-free real-time analysis and diagnosis of the CCRF-CEM tumor cells can be realized. In comparison with the detection principle of the CCRF-CEM tumor cells by the nucleic acid aptamer probe based on single fluorescence labeling illustrated in FIG. 3 of the drawings, whether there are target tumor cells or not in the system under detection, the fluorescence signal of the nucleic acid aptamer probe based on single fluorescence labeling can be detected, and the analysis of the target tumor cells should be carried out after a complex washing procedure, so that a real-time, effective, and fast detection of the target tumor cells can not be achieved.

Embodiment 2

Fluorescence Spectrum Characterization of the Switchable Nucleic Acid Aptamer Probe in a Buffer Four 200 μL buffer samples (Dulbecco's PBS, 4.5 g/L glucose, 5 mM $MgCl_2$, 1 mg/ml BSA) were respectively added with 100 nM switchable nucleic aptamer probe, switchable control nucleic acid probe, nucleic acid aptamer probe with single fluorescence labeling, and the control nucleic acid probe with single fluorescence labeling mentioned in the above first preferred embodiment. The four probes respectively have the following nucleotide sequences.

The switchable nucleic aptamer probe: SEQ ID NO: 1: [5'-(Cy5)-CTA ACC GT TTT TTT TTT TTT TTT TT ATC TAA CTG CTG CGC CGC CGG GAA AAT ACT GTA CGG TTA GA-(BHQ2)-3'];

The switchable control nucleic acid probe: SEQ ID NO: 2: [5'-(Cy5)-ACG GTT AG TTT TTT TTT TTT TTT TT ATA CGG TGA CGT CGC CGC CGG GAA AAT ACT GTC TAA CCG TA-(BHQ2)-3'];

The nucleic acid aptamer probe with single fluorescence labeling: SEQ ID NO: 3: [5'-(Cy5)-ATC TAA CTG CTG CGC CGC CGG GAA AAT ACT GTA CGG TTA GA-3'];

The control nucleic acid probe with single fluorescence labeling: SEQ ID NO: 4: [5'-(Cy5)-ATA CGG TGA CTG CGC CGC CGG GAA AAT ACT GTC TAA CCG TA-3'].

The buffers added with the above probes were stored overnight in a refrigerator at about 6° C., and after incubation at 6° C. until the fluorescence intensity was stable, the fluorescence spectrum (referring to curves a, b, c, e, and f in FIG. 4 of the drawings) was recorded by a fluorescence spectrophotometer (Hitachi Japan F-2500). The excitation wavelength was 620 nm and the emission wavelength was 640~740 nm.

Another two 200 μL above physiological buffers, serving as two supplement samples, were respectively added with 300 nM nucleic acid fragments SEQ ID NO: 9: (5'-TCT AAC CGT ACA GTA TTT TCC CGG CGG CGC AGC AGT TAG AT-3') which is completely complemented with the above nucleic acid aptamer probe fragment 11. Then 100 nM switchable nucleic aptamer probe and switchable control nucleic acid probe were respectively added into the two supplement samples. After uniformly mixed, stored overnight in a refrigerator at about 6° C., and then incubated at 6° C. until the fluorescence intensity was stable, the fluorescence spectrum (referring to curves d and g in FIG. 4 of the drawings) was recorded by the fluorescence spectrophotometer (Hitachi Japan F-2500). The excitation wavelength was 620 nm and the emission wavelength was 640~740 nm.

Figure 4:
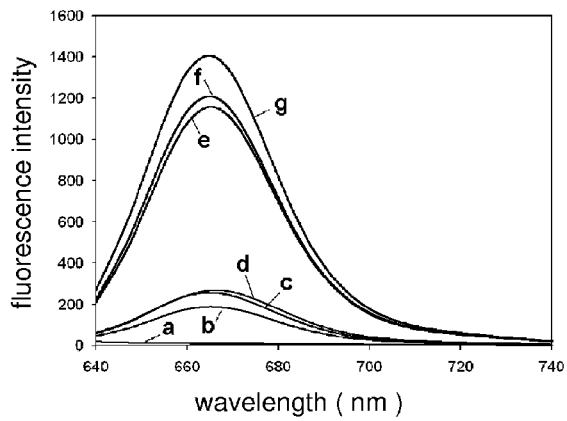
FIG. 4 is a fluorescence spectrum characterization diagram of different probes in different physiological buffer according to a second preferred embodiment of the present invention, wherein the curves from below to top respectively is the following fluorescence spectrum.

As illustrated in FIG. 4 of the drawings, when there are no targets in the blank control physiological buffers, the fluorescence signal of the switchable nucleic acid aptamer probe is significantly reduced and has a lower detection background in comparison with the nucleic acid aptamer probe with single fluorescence labeling and the control nucleic acid probe with single fluorescence labeling. Instead, when the switchable nucleic acid aptamer probe of the present invention is hybridized with the complementary sequence of the nucleic acid aptamer, the fluorescence of the switchable nucleic acid aptamer probe is greatly recovered and the signal intensity is higher than the nucleic acid aptamer probe with single fluorescence labeling.

Embodiment 3

Highly Specific Detection of Tumor Cells in a Buffer by the Switchable Nucleic Acid Aptamer Probe Two 200 μL buffer samples dispersed with $2\times10^5$ CCRF-CEM tumor cells were respectively added with 25 nM switchable nucleic aptamer probe and switchable control nucleic acid probe prepared in the second preferred embodiment. After uniformly mixed, and incubated for 15 min at room temperature in the dark, the fluorescence signal of the cells was immediately detected employing a FACSCalibur flow cytometry (Becton-Dickinson, US). In addition, buffers containing negative control cells such as Ramos cells, human multiple myeloma cells (U266 cells for short), B-lymphocytes of African marmosets (B95-8 cells for short), and etc. were respectively detected. The operation procedure was the same as above and the detection result of the buffers containing the four tumor cells is illustrated in FIG. 5. As shown in FIG. 5, the switchable nucleic aptamer probe and the switchable control nucleic acid probe cannot generate strong fluorescence signals for negative control cells such as Ramos cells, U266 cells, B95-8 cells and so on, but the switchable nucleic acid aptamer probe of the present invention represents a strong recovery of fluorescence after binding with the CCRF-CEM cells, while the switchable control nucleic acid probe still cannot generate stronger fluorescence signals. It proves the high specificity of different tumor cells by the switchable nucleic acid aptamer probe in this preferred embodiment.

Embodiment 4

A Comparison of Detection Sensitivity of Tumor Cells in the Buffer with the Switchable Nucleic Acid Aptamer Probe and the Conventional Art 200 μL buffer samples dispersed with $2\times10^5$ CCRF-CEM tumor cells were respectively added with 25 nM switchable nucleic aptamer probe, switchable control nucleic acid probe, nucleic acid aptamer probe with single fluorescence labeling, and control nucleic acid probe with single fluorescence labeling prepared in the second preferred embodiment. After uniformly mixed and then incubated for 15 min at room temperature in the dark, the fluorescence signal of the cells was immediately detected employing a FACSCalibur flow cytometry (Becton-Dickinson, US). The detection result is illustrated in FIG. 6. As shown in FIG. 6, the fluorescence intensity of the switchable control nucleic acid probe and the control nucleic acid probe with single fluorescence labeling are relatively weak, indicating that they could not specifically recognize the CCRF-CEM cells. But compared with the normal nucleic acid aptamer probe with single fluorescence group labeling, the switchable nucleic acid aptamer probe can generate a larger signal-to-background ratio under the same concentration of CCRF-CEM cells, so that the switchable nucleic acid aptamer probe is suitable to be employed for detection of target tumor cells of relatively low concentration.

Embodiment 5

Study of the Fluorescence Stability of the Switchable Nucleic Acid Aptamer Probe in the Serum 175 nM switchable nucleic acid aptamer probe and 2.25 μM random nucleic acid fragment SEQ ID NO: 10: (5-CTA ACC GTT TTT TTT TTT TTT TTT TAT CTA ACT GCT GCG CCG CCG GGA AAA TAC TGT AC-3') without any labeling were simultaneously added into 200 μL mouse serum. As incubated at 37° C., the fluorescence intensity was simultaneously monitored until it was stable using the fluorescence spectrophotometer (Hitachi Japan F-2500) with the excitation wavelength of 640 nm and the emission wavelength of 660 nm. The detection result is illustrated in FIG. 7. As shown in FIG. 7, with the prolonging of the incubation time, the fluorescence intensity of the switchable nucleic acid aptamer probe gradually increases. This is possibly resulted from degradation of the probe by the nuclease in the serum or conformation change due to the binding of some non-specific protein with the probe, so that the fluorescence is recovered to some extent. As indicated in FIG. 7, the half-life of the switchable nucleic acid aptamer probe in this preferred embodiment in the mouse serum at 37° C. is about 23 minutes, which is definitely enough to meet the requirement of in vivo and in vitro tumor detection.

Embodiment 6

Specific Detection of Tumor Cells in the Serum by the Switchable Nucleic Acid Aptamer Probe 200 μL mouse serum samples dispersed with $2\times10^5$ CCRF-CEM tumor cells were respectively added with 25 nM switchable nucleic aptamer probe and switchable control nucleic acid probe prepared in the second preferred embodiment. After uniformly mixed, and then incubated on ice for 30 min in the dark, the FACSCalibur flow cytometry (Becton-Dickinson, US) was employed to detect the fluorescence signal of the cells. In addition, the same operation was carried out for the mouse serum containing the Ramos cells. The final detection result is illustrated in FIG. 8. As shown in FIG. 8, even in the complex mixed system of serum, the switchable nucleic acid aptamer probe in this preferred embodiment still can realize the highly specific detection of the target CCRF-CEM cells.

Embodiment 7

Application of in vivo Detection of Tumors by the Switchable Nucleic Acid Aptamer Probe 200 μL suspensions dispersed with about $1\times10^7$ CCRF-CEM tumor cells were subcutaneously injected into the back of right forelegs of 3"4 weeks' old BALB/c male nude mice. After 3"4 weeks of growth, the tumors were significantly mature. Tumor-bearing nude mice with suitable sized tumors were randomly selected. About 140 μL physiological saline containing 4.5 nmol random nucleic acid fragment and 0.35 nmol switchable nucleic acid aptamer probe of the second preferred embodiment, was injected via tail vein (physiological saline containing the switchable control nucleic acid probe of the second preferred embodiment was used as control), and simultaneously a Maestro™ whole-body optical imaging system (CRI, US) was employed to monitor the fluorescence intensity of the sites of the tumors in real time. The conventional imaging method in comparison with the present invention was carried out as follows: 0.5 nmole nucleic acid aptamer probe with single fluorescence labeling of the second preferred embodiment was injected into the tumor-bearing nude mice via tail vein, and the other operation was the same as above.

The detection result of this preferred embodiment is illustrated in FIG. 9. As shown in FIG. 9, after injection into the CCRF-CEM tumor-bearing nude mice, the switchable control nucleic acid probe, which is designated as negative control, does not generate fluorescence signals observed at the sites of the tumors. Instead, after injection into the CCRF-CEM tumor-bearing nude mice, in about ten minutes the switchable nucleic acid aptamer probe generates fluorescence signals observed at the sites of the tumors. And with the time prolonging, the contrast ratio of the fluorescence signals of the sites with tumors to non-target tissue is gradually increased. After about 30 minutes, the sites with tumors still maintains a high contrast ratio of fluorescence signals, so that in vivo targeted imaging and detection to the target tumor cells is effectively achieved. In comparison, after the nucleic acid aptamer probe with single fluorescence labeling is injected into the CCRF-CEM tumor-bearing nude mice, the fluorescence signal is spread all over the body of the mice and gradually decreases with the time prolonging. Although the contrast ratio of the sites of tumors to the non-target tissue is slowly increased and becomes obvious after the time prolonged to 2 hours, but since the background is so high that the contrast ratio is significantly weaker than the switchable nucleic acid probe in this preferred embodiment. The detection time is very long and the imaging mechanism is relatively complicated, so that it is disadvantageous for the implement of early diagnosis of tumors.

Embodiment 8

Specificity Study of in vivo Detection of Tumors by the Switchable Nucleic Acid Aptamer Probe 200 µL suspensions dispersed with about 1×10$^7$ CCRF-CEM tumor cells were subcutaneously injected into the back of right forelegs of 3~4 weeks old BALB/c male nude mice. After 3~4 weeks of growth, the tumors were significantly mature. Another group of male nude mice injected with the Ramos cell suspensions was used as control. Two tumor-bearing nude mice with suitable sized of above tumors respectively were injected with about 140 µL physiological saline containing 4.5 nmol random nucleic acid fragment and 0.35 nmol switchable nucleic acid aptamer probe of the second preferred embodiment, via tail vein, and simultaneously the Maestro™ whole-body optical imaging system (CRI, US) was employed to monitor the fluorescence intensity of the sites of the tumors in real time. The detection result is illustrated in FIG. 10. As shown in FIG. 10, the switchable nucleic acid aptamer probe in this preferred embodiment holds a high specificity for in vivo detection of tumors and only generates fluorescence signals at the sites of CCRF-CEM tumors.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and are subject to change without departure from such principles. Therefore, this invention includes all modifications encompassed within the spirit and scope of the following claims.

---

What is claimed is:

1. The switchable nucleic acid aptamer probe, comprising:
a probe body comprising a nucleic acid aptamer fragment capable of specifically recognizing target tumor cells and a nucleic acid fragment capable of hybridizing with said nucleic acid aptamer fragment with a complementary sequence of 6~12 base pairs;
a flurorescence generating unit and a fluorescence quenching unit respectively connected to two ends of said switchable nucleic acid aptamer probe; and
a connecting fragment of a length of 7~15 nm connecting said nucleic acid aptamer fragment and said nucleic acid fragment to form a hairpin structure, wherein an ability of said nucleic acid fragment for competitively hybridizing with said nucleic acid aptamer fragment is weaker than an ability of said target tumor cells for interacting with said nucleic acid aptamer fragment, wherein said nucleic acid aptamer fragment is tumor-targeted nucleic acid aptamer selected from a technology of systematic evolution of ligands by exponential enrichment, wherein said nucleic acid aptamer fragment is selected from a group consisting of [a nucleic acid aptamer sequence 1 which is capable of specifically recognizing human T Cell acute lymphoblastic leukemia cell lines,] a nucleic acid aptamer sequence 1 which is capable of specifically recognizing Human Burkitt's lymphoma cell lines, and a nucleic acid aptamer sequence 2 which is capable of specifically recognizing mouse hepatoma cell lines;
[wherein a nucleotide sequence of said nucleic acid aptamer fragment 1 is:

SEQ ID NO: 3: 5'-ATC TAA CTG CTG CGC CGC CGG GAA AAT ACT GTA CGG TTA GA-3';]

wherein a nucleotide sequence of said nucleic acid aptamer fragment 1 is:

SEQ ID NO: 5: 5'-AAC ACC GTG GAG GAT AGT TCG GTG GCT GTT CAG GGT CTC CTC CCG GTG-3'; and wherein a nucleotide sequence of said nucleic acid aptamer fragment 2 is:

SEQ ID NO: 6: 5'-AGT CCA TTT TAT TCC GTT AAC CTC TGA ATA TTT ATG GAC-3'.

2. A switchable nucleic acid aptamer probe, comprising:
a probe body comprising a nucleic acid aptamer fragment capable of specifically recognizing target tumor cells and a nucleic acid fragment capable of hybridizing with said nucleic acid aptamer fragment with a complementary sequence of 6~12 base pairs;
a fluorescence generating unit and a fluorescence quenching unit respectively connected to two ends of said switchable nucleic acid aptamer probe; and a connecting fragment of a length of 7~15 nm connecting said nucleic acid aptamer fragment and said nucleic acid fragment to form a hairpin structure, wherein an ability of said nucleic acid fragment for competitively hybridizing with said nucleic acid aptamer fragment is weaker than an ability of said target tumor cells for interacting with said nucleic acid aptamer fragment, wherein said fluorescence generating unit is selected from a group consisting of fluorescence dye molecule and fluorescence nano-particle, wherein said fluorescence quenching unit is selected from a group consisting of fluorescence quenching group and functional nano-material having fluorescence quenching effect, wherein said nucleic acid aptamer fragment is tumor-targeted nucleic acid aptamer selected from a technology of systematic evolution of ligands by exponential enrichment, wherein said nucleic acid aptamer fragment is selected from a group consisting of [a nucleic acid aptamer sequence 1 which is capable of specifically recognizing human T Cell acute lymphoblastic leukemia cell lines,] a nucleic acid aptamer sequence 1 which is capable of specifically recognizing Human Burkitt's lymphoma cell lines, and a nucleic acid aptamer sequence 2 which is capable of specifically recognizing mouse hepatoma cell lines;
[wherein a nucleotide sequence of said nucleic acid aptamer fragment 1 is:

SEQ ID NO: 3: 5'-ATC TAA CTG CTG CGC CGC CGG GAA AAT ACT GTA CGG TTA GA-3';]

wherein a nucleotide sequence of said nucleic acid aptamer fragment 1 is:

SEQ ID NO: 5: 5'-AAC ACC GTG GAG GAT AGT TCG GTG GCT GTT CAG GGT CTC CTC CCG GTG -3'; and wherein a nucleotide sequence of said nucleic acid aptamer fragment 2 is:

SEQ ID NO: 6: 5'-AGT CCA TTT TAT TCC TGA ATA TTT GTT AAC CTC ATG GAC -3'.

3. A switchable nucleic acid aptamer probe, comprising:
a probe body comprising a nucleic acid aptamer fragment capable of specifically recognizing target tumor cells and a nucleic acid fragment capable of hybridizing with said nucleic acid aptamer fragment with a complementary sequence of 6~12 base pairs;
a fluorescence generating unit and a fluorescence quenching unit respectively connected to two ends of said switchable nucleic acid aptamer probe; and
a connecting fragment of a length of 7~15 nm connecting said nucleic acid aptamer fragment and said nucleic acid fragment to form a hairpin structure, wherein an ability of said nucleic acid fragment for competitively hybridizing with said nucleic acid aptamer fragment is weaker than an ability of said target tumor cells for interacting with said nucleic acid aptamer fragment, wherein said fluorescence generating unit is selected from a group consisting of fluorescence dye molecule and fluorescence nano-particle, wherein said fluorescence quenching unit is selected from a group consisting of fluorescence quenching group and functional nano-material having fluorescence quenching effect, wherein said fluorescence dye molecule is selected from a group consisting of fluorescein, rhodamine and Cy5, wherein said fluorescence nano-particle is selected from a group consisting of fluorescence dye-doped silica nano-particle and fluorescence quantum dot, wherein said fluorescence quenching group is selected from a group consisting of DABCYL, BHQ1 and BHQ2, wherein said functional nano-material having fluorescence quenching effect is selected from a group consisting of gold nano-particle and carbon nano-tube, wherein said nucleic acid aptamer fragment is tumor- targeted nucleic acid aptamer selected from a technology of systematic evolution of ligands by exponential enrichment, wherein said nucleic acid aptamer fragment is selected from a group consisting of [a nucleic acid aptamer sequence 1 which is capable of specifically recognizing human T Cell acute lymphoblastic leukemia cell lines,] a nucleic acid aptamer sequence 1 which is capable of specifically recognizing Human Burkitt's lymphoma cell lines, and a nucleic acid aptamer sequence 2 which is capable of specifically recognizing mouse hepatoma cell lines;
[wherein a nucleotide sequence of said nucleic acid aptamer fragment 1 is:

SEQ ID NO: 3: 5'-ATC TAA CTG CTG CGC CGC CGG GAA

AAT ACT GTA CGG TTA GA-3';]

wherein a nucleotide sequence of said nucleic acid aptamer fragment 1 is:

SEQ ID NO: 5: 5'-AAC ACC GTG GAG GAT AGT TCG GTG

GCT GTT CAG GGT CTC CTC CCG GTG -3'; and wherein a nucleotide sequence of said nucleic acid aptamer fragment 2 is:

SEQ ID NO: 6: 5'-AGT CCA TTT TAT TCC TGA ATA TTT

GTT AAC CTC ATG GAC -3'.

4. A switchable nucleic acid aptamer probe, comprising:
a probe body comprising a nucleic acid aptamer fragment capable of specifically recognizing target tumor cells and a nucleic acid fragment capable of hybridizing with said nucleic acid aptamer fragment with a complementary sequence of 6~12 base pairs;
a fluorescence generating unit and a fluorescence quenching unit respectively connected to two ends of said switchable nucleic acid aptamer probe; and
a connecting fragment of a length of 7~15 nm connecting said nucleic acid aptamer fragment and said nucleic acid fragment to form a hairpin structure, wherein an ability of said nucleic acid fragment for competitively hybridizing with said nucleic acid aptamer fragment is weaker than an ability of said target tumor cells for interacting with said nucleic acid aptamer fragment, wherein said connecting fragment is selected from a group consisting of a fragment not capable of hybridizing with said nucleic acid aptamer fragment or said nucleic acid fragment, and a fragment containing a polymer chain with hydrophilicity and biocompatibility, wherein said nucleic acid aptamer fragment is tumor-targeted nucleic acid aptamer selected from a technology of systematic evolution of ligands by exponential enrichment, wherein said nucleic acid aptamer fragment is selected from a group consisting of a nucleic acid aptamer sequence 1 which is capable of specifically recognizing human T Cell acute lymphoblastic leukemia cell lines, a nucleic acid aptamer sequence 1 which is capable of specifically recognizing Human Burkitt's lymphoma cell lines, and a nucleic acid aptamer sequence 2 which is capable of specifically recognizing mouse hepatoma cell lines;
[wherein a nucleotide sequence of said nucleic acid aptamer fragment 1 is:

SEQ ID NO: 3: 5'-ATC TAA CTG CTG CGC CGC CGG GAA

AAT ACT GTA CGG TTA GA-3';]

wherein a nucleotide sequence of said nucleic acid aptamer fragment 1 is:

SEQ ID NO: 5: 5'-AAC ACC GTG GAG GAT AGT TCG GTG

GCT GTT CAG GGT CTC CTC CCG GTG -3'; and wherein a nucleotide sequence of said nucleic acid aptamer fragment 2 is:

SEQ ID NO: 6: 5'-AGT CCA TTT TAT TCC TGA ATA TTT

GTT AAC CTC ATG GAC -3'.

5. A switchable nucleic acid aptamer probe, comprising:
a probe body comprising a nucleic acid aptamer fragment capable of specifically recognizing target tumor cells and a nucleic acid fragment capable of hybridizing with said nucleic acid aptamer fragment with a complementary sequence of 6~12 base pairs;
a fluorescence generating unit and a fluorescence quenching unit respectively connected to two ends of said switchable nucleic acid aptamer probe; and
a connecting fragment of a length of 7~15 nm connecting said nucleic acid aptamer fragment and said nucleic acid fragment to form a hairpin structure, wherein an ability of said nucleic acid fragment for competitively hybridizing with said nucleic acid aptamer fragment is weaker than an ability of said target tumor cells for interacting with said nucleic acid aptamer fragment, wherein said fluorescence generating unit is selected from a group consisting of fluorescence dye molecule and fluorescence nano-particle, wherein said fluorescence quenching unit is selected from a group consisting of fluorescence quenching group and functional nano-material having fluorescence quenching effect, wherein said connecting fragment is selected from a group consisting of a fragment not capable of hybridizing with said nucleic acid aptamer fragment or said nucleic acid fragment, and a fragment containing a polymer chain with hydrophilicity and biocompatibility, wherein said nucleic acid aptamer fragment is tumor-targeted nucleic acid aptamer selected from a technology of systematic evolution of ligands by exponential enrichment, wherein said nucleic acid aptamer fragment is selected from a group consisting of [a nucleic acid aptamer sequence 1 which is capable of specifically recognizing human T Cell acute lymphoblastic leukemia cell lines,] a nucleic acid aptamer sequence 1 which is capable of specifically recognizing Human Burkitt's lymphoma cell lines, and a nucleic acid aptamer sequence 2 which is capable of specifically recognizing mouse hepatoma cell lines;

[wherein a nucleotide sequence of said nucleic acid aptamer fragment 1 is:

SEQ ID NO: 3: 5'-ATC TAA CTG CTG CGC CGC CGG GAA AAT ACT GTA CGG TTA GA-3';]

wherein a nucleotide sequence of said nucleic acid aptamer fragment 1 is:

SEQ ID NO: 5: 5'-AAC ACC GTG GAG GAT AGT TCG GTG GCT GTT CAG GGT CTC CTC CCG GTG -3'; and wherein a nucleotide sequence of said nucleic acid aptamer fragment 2 is:

SEQ ID NO: 6: 5'-AGT CCA TTT TAT TCC TGA ATA TTT GTT AAC CTC ATG GAC -3'.

6. A switchable nucleic acid aptamer probe, comprising:
a probe body comprising a nucleic acid aptamer fragment capable of specifically recognizing target tumor cells and a nucleic acid fragment capable of hybridizing with said nucleic acid aptamer fragment with a complementary sequence of 6~12 base pairs;
a fluorescence generating unit and a fluorescence quenching unit respectively connected to two ends of said switchable nucleic acid aptamer probe; and
a connecting fragment of a length of 7~15 nm connecting said nucleic acid aptamer fragment and said nucleic acid fragment to form a hairpin structure, wherein an
ability of said nucleic acid fragment for competitively hybridizing with said nucleic acid aptamer fragment is weaker than an ability of said target tumor cells for interacting with said nucleic acid aptamer fragment, wherein said fluorescence generating unit is selected from a group consisting of fluorescence dye molecule and fluorescence nano-particle, wherein said fluorescence quenching unit is selected from a group consisting of fluorescence quenching group and functional nano-material having fluorescence quenching effect, wherein said fluorescence dye molecule is selected from a group consisting of fluorescein, rhodamine and Cy5, wherein said fluorescence nano-particle is selected from a group consisting of fluorescence dye-doped silica nano-particle and fluorescence quantum dot, wherein said fluorescence quenching group is selected from a group consisting of DABCYL, BHQ1 and BHQ2, wherein said functional nano-material having fluorescence quenching effect is selected from a group consisting of gold nano-particle and carbon nano-tube, wherein said connecting fragment is selected from a group consisting of a fragment not capable of hybridizing with said nucleic acid aptamer fragment or said nucleic acid fragment, and a fragment containing a polymer chain with hydrophilicity and biocompatibility, wherein said nucleic acid aptamer fragment is tumor-targeted nucleic acid aptamer selected from a technology of systematic evolution of ligands by exponential enrichment, wherein said nucleic acid aptamer fragment is selected from a group consisting of [a nucleic acid aptamer sequence 1 which is capable of specifically recognizing human T Cell acute lymphoblastic leukemia cell lines,] a nucleic acid aptamer sequence 1 which is capable of specifically recognizing Human Burkitt's lymphoma cell lines, and a nucleic acid aptamer sequence 2 which is capable of specifically recognizing mouse hepatoma cell lines;

[wherein a nucleotide sequence of said nucleic acid aptamer fragment 1 is:

SEQ ID NO: 3: 5'-ATC TAA CTG CTG CGC CGC CGG GAA AAT ACT GTA CGG TTA GA-3';]

wherein a nucleotide sequence of said nucleic acid aptamer fragment 1 is:

SEQ ID NO: 5: 5'-AAC ACC GTG GAG GAT AGT TCG GTG GCT GTT CAG GGT CTC CTC CCG GTG -3'; and wherein a nucleotide sequence of said nucleic acid aptamer fragment 2 is:

SEQ ID NO: 6: 5'-AGT CCA TTT TAT TCC TGA ATA TTT GTT AAC CTC ATG GAC -3'.

* * * * *